United States Patent [19]

Gaffar

[11] Patent Number: 4,590,064
[45] Date of Patent: May 20, 1986

[54] ANTICALCULUS ORAL COMPOSITION

[75] Inventor: Abdul Gaffar, Somerset, N.J.

[73] Assignee: Colgate-Palmolive Company, New York, N.Y.

[21] Appl. No.: 710,876

[22] Filed: Mar. 11, 1985

[51] Int. Cl.$^4$ .......................... A61K 7/16; A61K 7/18
[52] U.S. Cl. ........................................ 424/49; 424/52
[58] Field of Search ............................... 424/52, 49-58

[56] References Cited

U.S. PATENT DOCUMENTS

| | | | |
|---|---|---|---|
| 2,798,053 | 7/1957 | Brown | 260/2.2 |
| 2,923,692 | 2/1960 | Ackerman et al. | 260/17.4 |
| 2,980,655 | 4/1961 | Glass et al. | 260/80.3 |
| 3,923,876 | 12/1975 | Heins et al. | 260/502.4 R |
| 4,110,429 | 8/1978 | Gaffar et al. | 424/54 |
| 4,118,474 | 10/1978 | Gaffar et al. | 424/54 |
| 4,215,105 | 7/1980 | Gaffar et al. | 424/52 |
| 4,215,113 | 7/1980 | Eriksson et al. | 935/17 |
| 4,224,308 | 9/1980 | Gaffar et al. | 424/49 |
| 4,339,445 | 7/1982 | Erickssen et al. | 424/212 |

OTHER PUBLICATIONS

"A Comparison of Phosphonoacetic Acid and Phosphonoformic Acid Activity in Genital Herpes Simplex Virus Type 1 and 2 Infections of Mice", by E. R. Kern et al., in Antiviral Research, vol. 4, No. 1, pp. 225-235 (Nov. 1981).

Thorpe's Dictionary of Applied Chemistry, vol. 9, 4th Edition, pp. 510-511.

Primary Examiner—Shep K. Rose
Attorney, Agent, or Firm—Robert L. Stone; Herbert S. Sylvester; Murray M. Grill

[57] ABSTRACT

Oral compositions such as mouthwashes and toothpastes, creams, gels and powders containing as anticalculus agent phosphonoformic acid or salt thereof and optionally also an F-providing anticaries compound, and method of using such compositions.

11 Claims, No Drawings

ANTICALCULUS ORAL COMPOSITION

This invention relates to oral compositions containing an anticalculus agent.

Calculus is a hard, mineralized formation which forms on the teeth. Regular brushing aids in preventing a rapid build-up of these deposits, but even regular brushing is not sufficient to remove all of the calculus deposits which adhere to the teeth. Calculus is formed on the teeth when crystals of calcium phosphates begin to be deposited in the pellicle and extracellular matrix of the dental plaque and become sufficiently closely packed together for the aggregates to become resistant to deformation. There is no complete agreement on the route by which calcium and orthophosphate ultimately become the crystalline material called hydroxyapatite (HAP). It is generally agreed, however, that at higher saturations, that is, above the critical saturation limit, the precursor to crystalline HAP is an amorphous or microcrystalline calcium phosphate. "Amorphous calcium phosphate" although related to hydroxyapatite differs from it in atomic structure, particle morphology, and stoichiometry. The X-ray diffraction pattern of amorphous calcium phosphate shows broad peaks typical of amorphous materials, which lack the long-range atomic order characteristic of all crystalline materials, including HAP. It is apparent therefore that agents which effectively interfere with crystalline growth of HAP will be effective as anticalculus agents. A suggested mechanism by which the anticalculus agents of this invention inhibit calculus formation probably involves an increase of the activation energy barrier thus inhibiting the transformation of precursor amorphous calcium phosphate to HAP.

Studies have shown that there is a good correlation between the ability of a compound to prevent HAP crystalline growth in vitro and its ability to prevent calcification in vivo. See for example A. Gaffar et al, Calcified Tissue Research (1982):34:S8–S16.

A substantial number of different types of compounds and compositions have been developed for use as antibacterial, antiplaque, anticalculus agents in oral compositions, including for example such cationic materials as the bis-biguanide compounds and quaternary ammonium compounds, e.g. benzethonium chloride and cetyl pyridinium chloride, disclosed in U.S. Pat. No. 4,110,429. These cationic materials however tend to stain the teeth with continued use, and their antibacterial effect tends to disrupt or destroy the normal microflora of the mouth and/or digestive system.

A mumber of compounds containing one or more phosphono and/or carboxylic groups have been proposed as oral anticalculus agents, including for example 1-phosphonopropane tricarboxylic acid (PPT) in Heins, U.S. Pat. No. 3,923,876, ethylenediamine tetramethylenephosphonic acid (Editempa) in Kim, U.S. Pat. No. 4,143,128, 2-phosphonobutane-1,2,4-tricarboxylic acid (PBTA) in Gaffar, U.S. Pat. No. 4,224,308, and phosphonoacetic acid (PAA) in Gaffar, U.S. Pat. No. 4,215,105. Such agents however have been regarded as subject to one or more objectionable problems and disadvantages, with respect to availability, cost, unsatisfactory solubility, stability, sensory properties such as taste and smell, dermal or internal toxicity, dissolution or other damage to tooth surfaces, and/or incompatibility or interference with other functionally active or conventional additives in the oral composition. Illustratively, as shown hereinafter, such compounds as PPT and Editempa when employed in an oral composition together with a fluorine-providing anticaries compound interfere unduly with the desired anticaries effect and likely increase the rate of dissolution of tooth surfaces. On the other hand, PAA in an oral composition has been found to emit volatile osmophores providing an undesirable strong vinegary odor and a tart, sour taste generally objectionable and unacceptable to the prospective user.

It is an object of this invention to provide an improved anticalculus oral composition which will not be subject to one or more of the above problems and disadvantages.

A further object of the invention is to provide an oral composition which inhibits the transformation of amorphous calcium phosphate to HAP crystal structure normally associated with calculus.

Another object of this invention is the provision of an improved method for inhibiting the formation of calculus.

Other objects and advantages will appear as the description proceeds.

In accordance with certain of its aspects, this invention relates to an oral composition comprising an oral (orally acceptable) vehicle containing in an effective amount as an anticalculus agent phosphonoformic acid (PFA) of the formula: $H_2O_3P\text{-}COOH$, or an orally acceptable salt thereof, preferably water soluble, such as with an alkali metal (e.g. sodium and potassium), ammonium, $C_1$–$C_{18}$ mono-, di- and tri-substituted ammonium (e.g. alkanol substituted such as mono-, di- and triethanolammonium), or organic amine cation. A partially or completely neutralized salt may be employed, i.e. containing from 1 to 3 cations. The PFA compound may be anhydrous or hydrated. A preferred salt is the fully neutralized trisodium hexahydrate.

It is highly surprising that in contrast to the vinegary odor and tart sour taste of oral compositions containing the closely related PAA, those of the present invention containing PFA are comparatively odor-free and have a neutral to sweet taste, being also dermally milder.

U.S. Pat. No. 4,215,113 issued July 29, 1980 to B. Eriksson et al discloses compositions containing PFA, but those compositions are only intended, disclosed and claimed for the treatment of herpes and other viral infections. This patent fails to disclose, contemplate or suggest oral compositions and treatment processes of the type disclosed and claimed herein, namely compositions such as mouthwashes and toothpaste, gels and creams, the latter containing essential abrasive or polishing material, which compositions are normally used briefly (but regularly or daily) for washing, gargling or brushing teeth in the oral cavity and then promptly removed or released from the oral cavity by the user, usually by rinsing with water. The patent does however contain ample disclosures of physiologically acceptable salts of PFA (and methods of making them and PFA per se) which are operative in the oral compositions of this invention, and such disclosures are accordingly incorporated herein by reference thereto.

In an article entitled "A comparison of phosphonoacetic acid and phosphonoformic acid activity in genital herpes simplex virus type 1 and 2 infections in mice" by E. R. Kern et al in Antiviral Research, Vol. 4, #1 pp225–35 (Nov. 1981), PAA was apparently considered more antivirally active in certain respects than PFA, but the article further states that since PAA was precluded from clinical dermal use in humans and since PFA was already undergoing trials in patients with recurrent herpes labialis, the test results suggested that topical PFA deserved further evaluation in the treatment of mucocutaneous herpes simplex virus infections, including genital herpes. Like U.S. Pat. No. 4,215,113, this reference also fails to disclose or suggest application of its teachings to the preparation and use of oral compositions of the type disclosed and claimed herein, especially in view of the high (5%) concentration of PAA employed in the discussed dermal herpes tests relative to the much lower concentrations normally employed in mouthwashes, and toothpastes, gels and creams, at which lower concentrations objections to dermal use may be reduced, eliminated or not a problem facing the worker of ordinary skill in this art.

The concentration of the PFA compound (or salt) in the oral compositions can range widely, typically upward from about 0.01% by weight, with no upper limit on the amount that can be utilized except as dictated by cost or incompatibility with the vehicle. Generally, weight concentrations of about 0.01% to about 10%, and preferably about 0.1% to about 4%, more preferably about 0.2% to about 3% are utilized. Oral compositions which in the ordinary course of usage could be accidentally ingested preferably contain concentrations of the PFA compound in the lower portions of the foregoing ranges. Thus, a mouthwash in accordance with the invention preferably contains less than about 1.5% by weight of the PFA compound. Other dentifrice compositions, topical solutions and prophylactic pastes, the latter to be administered professionally, can preferably contain about 0.1% to 2% by weight of the PFA compound. The PFA compound should of course be compatible with the other components of the oral compositions of this invention.

The PFA compounds of this invention are anti-nucleating agents, oral compositions of this invention containing them are effective in reducing formation of dental calculus without unduly decalcifying or otherwise damaging or dissolving the dental enamel, and in contrast to the above-mentioned cationic antibacterial, antiplaque and anti-calculus agents, such PFA compounds and compositions have little or no tendency to stain the teeth.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to to alcohol is in the range of from about 1:1 to about 20:1, preferably about 3:1 to 10:1 and more preferably about 4:1 to about 6:1. The total amount of water-alcohol mixture in this type of preparation is typically in the range of from about 70% to about 99.9% by weight of the preparation.

The pH of such liquid and other preparations of the invention is generally in the range of from about 4.5 to about 9 and typically from about 5.5 to 8. The pH is preferably in the range of from about 6 to about 8.0. It is noteworthy that the compositions of the invention may be applied orally at a pH below 5 without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In certain other desirable forms of this invention, the oral composition may be substantially solid or pasty in character, such as toothpowder, a dental tablet, a toothpaste, gel or dental cream. The vehicle of such solid or pasty oral preparations generally contains polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, aluminum silicate, zirconium silicate, urea formaldehyde, silica, bentonite, and mixtures thereof. Preferred polishing materials include crystalline silica having particle sizes of up to about 5 microns, a mean particle size of up to about 1.1 microns, and a surface area of up to about 50,000 $cm.^2/gm.$, silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100 and alkali metal alumino-silicate complexes are particularly useful, since they have refractive indices close to the refractice indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner, as illustrated by Thorpe's *Dictionary of Applied Chemistry*, Volume 9, 4th Edition, pp. 510–511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than about 1% of the material is larger than about 37 microns.

The polishing material is generally present in the solid or pasty compositions in weight concentrations of about 10% to about 99%. Preferably, it is present in amounts ranging from about 10% to about 75% in toothpaste, and from about 70% to about 99% in toothpowder.

In a toothpaste, the liquid vehicle may comprise water and humectant typically in an amount ranging from about 10% to about 90% by weight of the preparation. Glycerine, propylene glycol, sorbitol, polypropylene glycol and/or polyethylene glycol (e.g. 400,600) exemplify suitable humectants/carriers. Also advantageous are liquid mixtures of water, glycerine and sorbitol, In clear gels where the refractive index is an important consideration, about 3-30 wt. % of water, 0 to about 80 wt. % of glycerine, and about 20-80 wt. % of sorbitol is preferably employed.

Toothpastes, creams and gels typically contain a natural or synthetic thickener or gelling agent in proportions of about 0.1 to about 10, preferably about 0.5 to about 5, wt. %. A suitable thickener is synthetic hectorite, a synthetic colloidal magnesium alkali metal silicate complex clay available for example as Laponite (e.g. CP, SP 2002, D) marketed by Laporte Industries Limited. Laponite D analysis shows, approximately by weight, 58.00% $SiO_2$, 25.40% MgO, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners include Irish moss, gum tragacanth, starch, polyvinylpyrrolidone, hydroxyethypropylcellulose, hydroxybutyl methyl cellulose, hydroxypropyl methyl cellulose, hydroxyethyl cellulose (e.g. available as Natrosol), sodium carboxymethyl cellulose, poly(methyl vinyl ether/maleic anhydride) available for example as Gantrez AN 139 (GAF Corporation), colloidal silica such as finely ground Syloid (e.g. 244), and carboxyvinyl polymer for example available as Carbopol (e.g. 934, 940, 941). These Carbopol products of B. F. Goodrich Co. are described in U.S. Pat. Nos. 2,798,053, 2,923,692 and 2,980,655, being essentially colloidally water-insoluble acidic carboxylic polymers of acrylic acid cross-linked with about 0.75 to about 2.0% of a cross-linking agent of polyallyl sucrose or polyallyl pentaerythritol.

It will be understood that, as is conventional, the oral preparations are to be sold or otherwise distributed in suitable labelled packages. Thus a jar of mouthrinse will have a label describing it, in substance, as a mouthrinse or mouthwash and having directions for its use; and a toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions. Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

In certain preferred forms of this invention a fluorine-providing anti-caries compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, calcium fluoride, a copper fluoride such as cuprous fluoride, zinc fluoride, a tin fluoride such as stannic fluoride or stannous chlorofluoride, barium fluoride, sodium fluorsilicate, ammonium fluorosilicate, sodium fluorozirconate, sodium monofluoro-phosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of the fluorine-providing compound is dependent to some extent upon the type of compound, its solubility, and the type of oral preparation, but it must be a nontoxic amount, generally about 0.01 to about 3.0% in the preparation. In a solid oral preparation, e.g. gel, toothpaste or toothpowder, an amount of such compound which releases up to about 1% F ion by weight of the preparation is considered satisfactory. Any suitable minimum amount of such compound may be used, but it is preferable to employ sufficient compound to release about 0.005% to 1%, more preferably about 0.1% of fluoride ion. Typically, in the cases of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount of about 0.1-3.0%, more typically about 0.76%.

In a liquid oral preparation such as a mouthwash, the flourine-providing compound is typically present in an amount sufficient to release up to about 1.0%, preferably about 0.001% to 0.5%, by weight of fluoride ion. Generally about 0.01 to about 3.0 wt. % of such compound is present.

Various other materials may be incorporated in the oral preparations of this invention such as whitening agents, preservatives, silicones, chlorophyll compounds, other anticalculus agents, antibacterial antiplaque agents, and/or ammoniated material such as urea, diammonium phosphate, and mixtures thereof. These adjuvants, where present, are incorporated in the preparations in amounts which do not substantially adversely affect the properties and characteristics desired.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, APM (aspartyl phenyl alanine, methyl ester), saccharine and the like. Suitably, flavor and sweetening agents may together comprise from about 0.01% to 5% or more of the preparation.

In preparing the oral compositions of this invention, it is preferred but not essential to add the PFA after the other ingredients (except perhaps some of the water) are mixed or contacted with each other to avoid a tendency for the PFA to be precipitated.

For instance, a mouthrinse or mouthwash may be prepared by mixing ethanol and water with surfactant, humectant, gum or thickener such as sodium carboxymethylcellulose or hydroxyethyl cellulose, and sweetener and adding thereto flavor, additional water, and then the PFA compound. A toothpaste may be prepared by forming a gel with humectant, gum or thickener such as sodium carboxymethyl cellulose or hydroxyethyl cellulose, and sweetener and adding thereto polishing agent, flavor, additional water and then the PFA compound.

In the practice of this invention an oral composition according to this invention such as a mouthwash or toothpaste containing the PFA compound in an amount effective to inhibit calculus on dental surfaces is preferably applied regularly to dental enamel, such as every second or third day or preferably from 1 to 3 times daily, at a pH of about 4.5 to a about 9, generally about 5.5 to about 8, preferably about 6 to 8, for at least 2 weeks up to 8 weeks or more up to lifetime.

The PFA compound can be incorporated in chewing gum or other products, e.g. by stirring into a warm gum base or coating the outer surface of a gum base, illustrative of which may be mentioned jelutone, rubber latex, vinylite resins, etc., desirably with conventional plasticizers or softeners, sugar or other sweeteners or carbohydrates such as glucose, sorbitol and the like.

The following examples are further illustrative of the nature of the present invention, but it is understood that the invention is not limited thereto. All amounts and proportions referred to herein and in the appended claims are by weight and temperatures are in degrees C. unless otherwise indicated.

EXAMPLE 1

Inhibition of Crystal Growth of HAP

This is evaluated by a pH Stat method. 1.0 ml of an aqueous solution of $1 \times 10^{-4}M$ to $1 \times 10^{-5}M$ of the anticalculus agent being tested and 0.1M sodium dihydrogen phosphate is placed in a reaction flask with 22 to 23 ml. of distilled water with continuous stirring in an atmosphere of nitrogen. To this is added 1 ml. of 0.1M $CaCl_2$ and the pH adjusted to $7.4 \pm 0.05$ with NaOH (final conc. of $Ca^{++}$ and $PO_4^{3-} = 4 \times 10^{-3}M$). Consumption of 0.1N NaOH is recorded automatically by a pH Stat (Radiometer). In this test, the formation of HAP occurs in 2 distinct phases. First rapid base consumption (1–4 min.) takes place which then diminishes until 15–20 minutes when second rapid uptake takes place. A delay in the time of second rapid consumption indicates an interference with the crystal growth of HAP. Agents which interfere with HAP crystal growth are effective anticalculus agents. When PFA is tested by the foregoing procedure, the following results are obtained.

TABLE 1

| Anticalculus Agent (conc) | Time for HAP Formation (Min.) | Delay in HAP Formation (Min.) |
|---|---|---|
| Water (control) | 17.4 | — |
| PFA (10 ppm) | 18.0 | — |
| PFA (20 ppm) | 25.0 | 7.6 |
| PFA (40 ppm) | >37 | 19.6 |

The above results show that PFA effectively inhibits crystal growth of HAP in vitro and that the inhibition is not due to complexation or chelation of calcium since sub-stoichiometric ratios of PFA:calcium are employed.

The following examples are illustrative of mouthwash formulations according to the invention, to be used in the normal manner, e.g. contacting the teeth in the oral cavity substantially regularly, e.g. several weeks or more up to a lifetime or until an anticalculus effect is no longer desired or necessary, in each case followed by removing the mouthwash from the oral cavity (without ingestion) as by rinsing with water.

|  | Example | | | |
|---|---|---|---|---|
|  | 2 | 3 | 4 | 5 |
| Flavor | 0.22% | 0.22% | 0.22% | 0.22% |
| Ethanol | 15.0 | 15.0 | 15.0 | 15.0 |
| Pluronic F108* | 3.0 | 3.0 | 3.0 | 3.0 |
| Glycerine | 10.0 | 10.0 | 10.0 | 10.0 |
| Na Saccharin | 0.03 | 0.03 | 0.03 | 0.03 |
| NaF | 0.22 | — | — | — |
| MFP** | — | — | 0.76 | — |
| PFA*** | 0.1 | 0.5 | 1.0 | 1.5 |
| Water q.s. to | 100 | 100 | 100 | 100 |
| pH (with NaOH) | 7.4 | 7.4 | 7.4 | 7.4 |
| Appearance | Clear | Clear | Clear | Clear |

*Approx. 20% polyoxypropylene M.W:3250/80% polyoxyethylene block polymer nonionic surfactant - BASF-Wyandotte
**Sodium monofluoro phosphate
***Trisodium hexahydrate salt The following examples are illustrative of anticalculus toothpastes according to the invention, to be used in the normal manner, e.g. brushing the teeth with the toothpaste substantially regularly, e.g. 1 to 3 times daily or every 2nd or 3rd day for several weeks or more up to lifetime or until an anticalculus effect is no longer desired or necessary, in each case followed by removing the toothpaste from the oral cavity (without ingestion) as by rinsing with water.

|  | Example | |
|---|---|---|
|  | 6 | 7 |
| MFP | 0.76% | — |
| Sodium lauryl sulfate | 1.5 | 1.5% |
| Silica | 30.0 | 30.0 |
| Glycerine | 25.0 | 25.0 |
| Sodium benzoate | 0.5 | 0.5 |
| TiO2 | 0.4 | 0.4 |
| Nacarboxymethyl cellulose | 1.3 | 1.3 |
| PFA* | 1.0 | 1.0 |
| Sodium saccharin | 0.2 | 0.2 |
| Flavor | 1.0 | 1.0 |
| Water q.s. to | 100 | 100 |

*Trisodium hexahydrate salt

The dentifrice in Example 7 was extracted with water as follows: 10 grams of the dentifrice were mixed with 30 grams of deionized distilled water. After 5-10 minutes mixing, the slurry was centrifuged. The supernatants, water soluble fractions, were tested in the hydroxyapatite (HAP) formation test as described in Example 1. A placebo dentifrice without PFA was also used as a control. The data results are summarized in Table 2.

rate and fluoride content were assessed according to routine procedures. The results are shown in Table 3.

TABLE 3

Average per rat (N = 12) of smooth surface plaque extent (PE), initial - (T) and advanced - (B) dentinal fissure carious lesions, smooth surface caries units (E), weight gains (g), dissolution rate ($\mu$gP), and fluoride concentration in the first (I), the second (II) and the first and second layers (I & II) commulated.

| | Test Solution | PE* | T** | B** | E*** | g | $\mu$gP | ppm F in layers I | II | I & II |
|---|---|---|---|---|---|---|---|---|---|---|
| 1 | Control, $H_2O$ | 2.3 | 8.1 | 2.7 | 10.8 | 78 | 158 | 46 | 19 | 32 |
| 2 | 300 ppm $F^-$ (NaF) | 2.3 | 5.8 | 1.0 | 4.0 | 80 | 130 | 263 | 75 | 169 |
| 3 | 0.82% PPT | 2.5 | 8.3 | 2.5 | 10.2 | 77 | 151 | 46 | 22 | 34 |
| 4 | 0.82% PPT and 300 ppm $F^-$ | 2.2 | 6.3 | 1.3 | 5.3 | 79 | 139 | 188 | 69 | 128 |
| 5 | 0.82% PFA | 2.4 | 7.7 | 1.9 | 12.4 | 76 | 152 | 60 | 28 | 44 |
| 6 | 0.82% PFA and 300 ppm $F^-$ | 2.1 | 6.0 | 1.1 | 3.9 | 77 | 129 | 207 | 71 | 139 |
| 7 | 0.82% Editempa | 2.3 | 7.1 | 1.4 | 6.3 | 84 | 155 | 44 | 19 | 31 |
| 8 | 0.82% Editempa and 300 ppm $F^-$ | 2.1 | 6.5 | 1.0 | 3.7 | 77 | 142 | 159 | 55 | 107 |
| $S_{\bar{x}}$ | Standard error of the means | 0.20 | 0.70 | 0.49 | 1.34 | 3.6 | 3.9 | 18.7 | 6.8 | 12.2 |
| $S_{\bar{d}}$ | Standard error of the difference between two means | 0.29 | 1.00 | 0.70 | 1.89 | 5.2 | 5.5 | 26.4 | 9.6 | 17.2 |
| | PF < | NS | 0.001 | 0.01 | 0.001 | NS | 0.001 | 0.001 | 0.001 | 0.001 |
| | LSD 0.05 | 0.57 | 1.98 | 1.38 | 3.76 | 10.2 | 11.0 | 52.4 | 19.0 | 34.2 |
| | LSD 0.01 | 0.75 | 2.62 | 1.83 | 4.98 | 13.6 | 14.6 | 69.5 | 25.2 | 45.3 |
| | LSD 0.001 | 0.97 | 3.39 | 2.37 | 6.44 | 17.5 | 18.8 | 89.8 | 32.6 | 58.6 |

*4 units at risk,
**12 fissures at risk,
***20 units at risk,
LSD = least significant difference

TABLE 2

| Treatment | Conc. of HAP in Extracts | Time for HAP Formation (Min.) | Delay in HAP Formation (Min.) |
|---|---|---|---|
| Water | — | 18.3 | — |
| Placebo Toothpaste Extract | — | 22.5 | 4.2 |
| Active Toothpaste Extract | 20* ppm | 39.0 | 20.7 |

*Calculated from dilution factor of the extract.

The data in the table indicates that PFA incorporated in a specific dentifrice maintained anticalculus effect since the extract containing PFA was effective in inhibiting HAP formation.

EXAMPLE 8

In Vivo Test With Fluoride

The purpose of the present study was to test the effect in rats of topical application of 1-phosphonopropane tricarboxylic acid (PPT), phosphonoformic acid (PFA), sodium fluoride (NaF) and Editempa on plaque extent, fissure and smooth surface caries incidence, molar surface dissolution rate and fluoride content. The animals received ad libitum tap water and a cariogenic diet (2000a) containing 56% sucrose. In this study 12 litters of OM-rats, each litter consisting of 9 animals were used.

On day 13 the animals with their dams were transferred to stainless-steel, screen-bottom cages and fed finely powdered Nafag stock diet and tap water ad libitum until day 20. Then they were distributed at random among the treatments and received the cariogenic diet and tap water ad libitum. On the days 21 and 22 they were inoculated twice daily with heavy suspensions of S. mutans OMZ-176 and A. viscosus Ny-1. For 20 days from day 23 onwards, 100 microliters of the test solutions 1-8 listed in Table 3 below were applied with disposable syringes, twice daily. Plaque extent, caries of fissures and smooth surfaces, molar surface dissolution The results in Table 3 establish the overall superiority of PFA relative to PPT and Editempa anticalculus agents when applied in combination with F-containing anticaries agent. The results show that although no significant differences were found among the test solutions with respect to smooth surface plaque extent (PE) and weight gains, the PFA/F solution exhibited significantly less interference to the anticaries, antidissolution, and F impregnation functions of the F-containing agent relative to the PPT/F and Editempa/F solutions. Thus, as to anticaries effects, initial lesions (T) were reduced from 8.1 (control) to 5.8 by the F (NaF) solution and to almost the same degree (6.0) by the PFA/F solution, but to only 6.3 by the PPT/F solution and 6.5 by the Editempa/F solution. The reductions in advanced lesions (B) from 2.7 (control) to 1.0 and in smooth surface caries (E) from 10.8 (control) to 4.0 by the F solution were substantially matched by the 1.1B and 3.9E of the PFA/F solution and the 1.0B and 3.7E of the Editempa/F solution, but not by the PPT/F solution (1.3B & 5.3E).

The superiority of PFA is even more pronounced with respect to minimizing the rate of dissolution of dental surfaces ($\mu$gP). The control rate of 158 was reduced in almost identical amount by the F solution (130) and the PFA/F solution (129), in contrast to the effects of the PPT/F solution (139) and the Editempa/F solution (142).

The substantial superiority of PFA is also apparent with respect to maximizing (i.e. minimizing reduction of) the amount of anticaries F impregnation into layers I and II of the teeth produced by the F (NaF) solution. Whereas the F solution produced 169 ppm F in layers I and II compared to 32 ppm F produced by the control, the PFA/F solution produced 139 ppm F in these layers while the PPT/F solution produced only 128 ppm F and the Editempa/F solution was even more inferior, producing only 107 ppm F in these layers.

This invention has been described with respect to preferred embodiments and it will be understood that modifications and variations thereof obvious to those skilled in the art are to be included within the spirit and purview of this application and the scope of the appended claims.

What is claimed is:

1. In a method of effectively inhibiting crystal growth of hydroxyapatite associated with calculus by employing on teeth, without substantially decalcifying or otherwise damaging dental enamel, phosphono and carboxylic group-containing compounds, the improvement characterized by the step of contacting the teeth in the oral cavity and then removing an oral mouthwash, toothpaste, gel or cream composition comprising an orally acceptable vehicle having a pH of about 4.5 to about 9, said composition being selected from the group consisting of such:

A. Compositions containing in an effective amount, in the range of about 0.01% to about 10% by weight, as an anticalculus agent phosphonoformic acid or an orally acceptable salt thereof, and an effective anticaries amount, in the range of about 0.01% to about 3.0% by weight, of a fluorine-providing anticaries compound, and B. Compositions containing in an effective amount, in the range of about 0.01% to about 10% by weight, as an anticalculus agent phosphonoformic acid or an orally acceptable salt thereof, and devoid of an effective anticaries amount of a fluorine-providing anticaries compound.

2. The teeth contacting method of claim 1 employing the trisodium hexahydrate salt of phosphonoformic acid as anticalculus agent.

3. The teeth contacting method of claim 2 employing in an effective anticaries amount a fluorine-providing anticaries compound.

4. The teeth contacting method of claim 1 employing in an effective anticaries amount a fluorine-providing anticaries compound.

5. The teeth contacting method of claim 1 employing about 0.1% to about 4% by weight of said agent.

6. The oral composition of claim 1 containing about 0.01% to about 10% by weight of said agent.

7. The teeth contacting method of claim 1 wherein said vehicle comprises water and alcohol and said composition is a mouthwash.

8. The teeth contacting method of claim 1 wherein said vehicle comprises a liquid vehicle, a gelling agent and a dentally acceptable polishing material, and said composition is a toothpaste.

9. The teeth contacting method of claim 8 comprising brushing teeth with said toothpaste composition and then promptly removing said composition from the teeth.

10. The teeth contacting method of claim 1 wherein said composition further contains about 0.01% to about 5% by weight of combined flavor and sweetening agents.

11. The teeth contacting method of claim 1 wherein said vehicle has a pH of about 6 to about 8.

* * * * *